United States Patent
Baumann et al.

(10) Patent No.: US 6,207,461 B1
(45) Date of Patent: Mar. 27, 2001

(54) PROCESS FOR THE PREPARATION OF PLATINUM OR PALLADIUM BENZOPORPHYRINS AND PLATINUM OR PALLADIUM CYCLOHEXENOPORPHYRINS, INTERMEDIATES, AND AN OXYGEN SENSOR COMPRISING PLATINUM OR PALLADIUM CYCLOHEXENOPORPHYRIN

(75) Inventors: Marcus Baumann, Basel; Adrian Waldner, Allschwil, both of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/230,211

(22) PCT Filed: Jul. 21, 1997

(86) PCT No.: PCT/EP97/03915

§ 371 Date: Jan. 21, 1999

§ 102(e) Date: Jan. 21, 1999

(87) PCT Pub. No.: WO98/03512

PCT Pub. Date: Jan. 29, 1998

(30) Foreign Application Priority Data

Jul. 22, 1996 (CH) .................................................. 1831/96

(51) Int. Cl.$^7$ .......................... G01N 31/00; G01N 21/76; C07B 47/00; C07D 487/22
(52) U.S. Cl. ....................... 436/136; 436/127; 436/172; 540/145
(58) Field of Search .................................. 436/172, 127, 436/136; 540/145

(56) References Cited

U.S. PATENT DOCUMENTS

| | | | | |
|---|---|---|---|---|
| 4,810,655 | * | 3/1989 | Khalil et al. ........................... | 436/138 |
| 5,043,286 | * | 8/1991 | Khalil et al. ........................... | 436/136 |
| 5,399,583 | * | 3/1995 | Levy et al. ........................... | 514/410 |
| 5,837,865 | * | 11/1998 | Vinogradov et al. ................ | 540/145 |
| 5,863,460 | * | 1/1999 | Slovacek et al. ............... | 252/301.35 |

FOREIGN PATENT DOCUMENTS

| | | |
|---|---|---|
| 2132348 | 7/1984 | (GB) . |
| 9510522 | 4/1995 | (WO) . |

OTHER PUBLICATIONS

Medforth et al., "Tetracycloalkenyl–Meso–Tetraphenylporphyrins as Models for the Effect of Non–Planarity on the Light Absorption Properties of Photosynthetic Chromophores," Tetrahedron Letters, vol. 31, No. 26, 1990, pp. 3719–3722.

Aartsma et al., "Porphyrins. 43. Triplet Sublevel Emission of Platinum Tetrabenzoporphyrin by Spectrothermal Principal Component Decomposition," J. Am. Chem. Soc., vol. 104, No. 23, 1982, pp. 6278–6283.

May et al., "Porphyrins with Exocyclic Rings. 2. Synthesis of Geochemically Significant Tetrahydrobenzoporphyrins from 4,5,6,7–Tetrahydro–2H–isoindoles," J. Org. Chem., vol. 57, 1992, pp. 4820–4828.

Papkovsky et al., "Phosphorescent polymer films for optical oxygen sensors," Biosensors & Bioelectronics, vol. 7, 1991, pp. 199–206.

* cited by examiner

Primary Examiner—Maureen M. Wallenhorst
Assistant Examiner—LaToya I. Cross
(74) Attorney, Agent, or Firm—Wenderoth, Lind & Ponack, L.L.P.

(57) ABSTRACT

Compounds of formula (I) wherein Me is Pd(II) or Pt(II); R is H or $C_1$–$C_{18}$ alkyl, or is $C_3$–$C_8$ cycloalkyl, phenyl, pyridyl or phenyl-$C_1$–$C_4$ alkylene, each of which is unsubstituted or substituted by $C_1$–$C_{18}$ alkyl, $C_1$–$C_{18}$ alkoxy, $R_3$—O—C (O)—, halogen, —CN or by —$NO_2$; $R_1$ and $R_2$ are each independently of the other H, $C_1$–$C_{12}$ alkyl or $C_1$–$C_{12}$ alkoxy or $R_1$ and $R_2$ together are —$OCH_2O$—, —$OCH_2CH_2O$—, or —CH=CH—CH=CH—, and $R_3$ is $C_1$–$C_{18}$ alkyl, $C_3$–$C_{18}$ cycloalkyl, phenyl, benzyl, $C_1$–$C_{12}$ alkylphenyl or $C_1$–$C_{12}$ alkylbenzyl. Compounds of formula (I) are valuable luminophores and/or intermediates for the preparation of palladium (II) or platinum (II) benzoporphyrins, which are likewise luminophores.

(I)

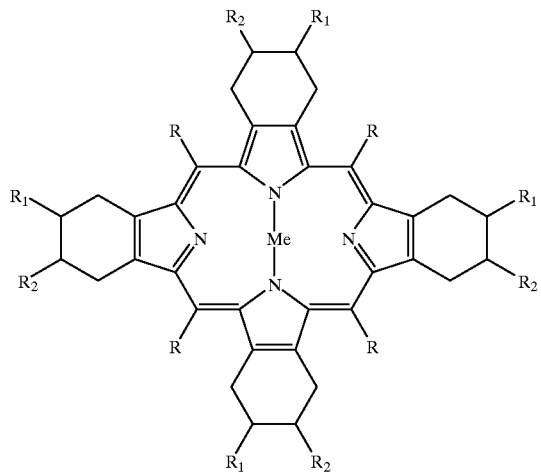

18 Claims, No Drawings

PROCESS FOR THE PREPARATION OF PLATINUM OR PALLADIUM BENZOPORPHYRINS AND PLATINUM OR PALLADIUM CYCLOHEXENOPORPHYRINS, INTERMEDIATES, AND AN OXYGEN SENSOR COMPRISING PLATINUM OR PALLADIUM CYCLOHEXENOPORPHYRIN

This application is a 371 of PCT/EP97/03915 filed on Jul. 21, 1997 and claiming priority of Switzerland application 1831/96 filed on Jul. 22, 1996.

The present invention relates to a process for the preparation of platinum and palladium benzoporphyrins and platinum or palladium cyclohexenoporphyrins by reacting unsubstituted or substituted cyclohexenoporphyrins in a polar solvent with complexed platinum or palladium salts at elevated temperatures; to novel palladium and platinum cyclohexenoporphyrins; to coating compositions comprising palladium and platinum cyclohexenoporphyrins; to oxygen sensors comprising palladium or platinum cyclohexenoporphyrins; and to the use of palladium and platinum cyclohexenoporphyrins as fluorescence indicators for the qualitative or quantitative determination of oxygen in gases or liquids.

Platinum(II) and palladium(II) porphyrins are suitable as phosphorescence dyes for the optical determination of physiological oxygen concentrations in cells or blood because they have absorption bands in the visible range and emission bands in the long-wave range, especially emission bands in the NIR range, and the phosphorescence radiation can therefore be excited and measured directly in the blood or in cells. Furthermore, they are distinguished by advantageous decay times in the excited state, which are in the microsecond range. Those properties are described by D. B. Papovsky et at in Biosensors & Bioelectronics 7 (1991), pages 199 to 206.

In J. Am. Chem. Soc., Vol. 104, No. 23, pages 6278 to 6283, T. J. Aartsma et al describe a process for the preparation of platinum(II) tetrabenzoporphyrin by adding tetrabenzoporphyrin to a boiling solution of $PtCl_2$ in benzonitrile using an extraction apparatus. No yields are given. The re-working of that process gives, after the specified reaction time of 48 hours, a contaminated crude product in a yield of only 6.5%, which can be purified to a usable phosphorescence dye only by repeated chromatography, in a correspondingly lower yield. That preparation process is therefore of no interest at all from the point of view of economics.

WO 95/10522 discloses metal porphyrins as phosphorescence indicators in oxygen sensors. In order to prepare the metal porphyrins, for example palladium tetraphenylbenzoporphyirn, it is proposed to react tetraphenylbenzoporphyrin with $Pd(CH_3CO_2)_2$ in an imidazole melt at up to 250° C. Although good yields are achieved, melt processes are difficult to carry out and are uneconomic on an industrial scale.

Surprisingly, it has now been found that, in contrast to benzoporphyrins, tetracyclohexenoporphyrins are reacted in the presence of nitrites with platinum or palladium salts in considerably shorter reaction times and with better yields and high purities. Furthermore, it has been found, surprisingly, that the reaction times can be shortened further if dinitrile complexes of platinum or palladium salts are used. It has also been found, surprisingly, that representatives of the novel class of the tetracyclohexenoporphyrins are also excellent phosphorescence indicators for the optical detection of oxygen because they exhibit high phosphorescence yields of around 42% and advantageous decay times in their excited state of around 80 µs. It has also been found that tetracyclohexenoporphyrins can be converted surprisingly readily into the corresponding tetrabenzoporphyrins by dehydrogenation, and simple preparation is thus possible even on an industrial scale. The tetracyclohexenoporphyrins forming the novel class are, therefore, valuable intermediates for the preparation of tetrabenzoporphyrins, especially tetraphenyltetrabenzoporphyrins. The invention relates firstly to compounds of formula I

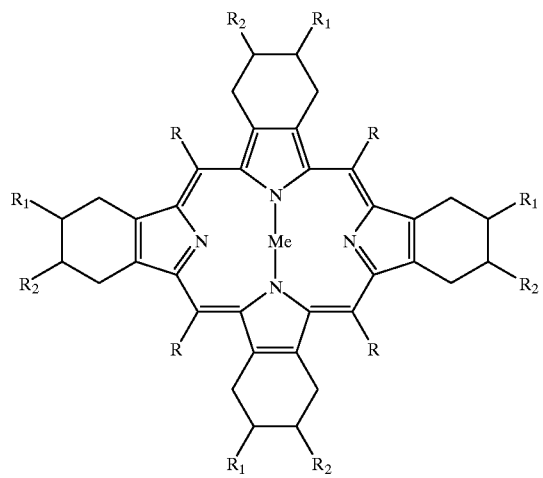

(I)

wherein

Me is Pd(II) or Pt(II);

R is H or $C_1$–$C_{18}$alkyl, or is $C_3$–$C_8$cycloalkyl, phenyl, pyridyl or phenyl-$C_1$–$C_4$alkylene, each of which is unsubstituted or substituted by $C_1$–$C_{18}$alkyl, $C_1$–$C_{18}$alkoxy, $R_3$—O—C(O)—, halogen, —CN or by —$NO_2$;

$R_1$ and $R_2$ are each independently of the other H, $C_1$–$C_{12}$alkyl or $C_1$–$C_{12}$alkoxy, or $R_1$ and $R_2$ together are —$OCH_2O$—, —$OCH_2CH_2O$— or —CH=CH—CH=CH—; and $R_3$ is $C_1$–$C_{18}$alkyl, $C_3$–$C_8$cycloalkyl, phenyl, benzyl, $C_1$–$C_{12}$alkylphenyl or $C_1$–$C_{12}$alkylbenzyl.

In formula I, Me is preferably Pt(II).

The substituents in the cyclic radicals of R, for example cyclohexyl or phenyl, may be bonded in the 2-, 3- or 4-position. The radicals are preferably monosubstituted, with the substituent being bonded especially in the 4-position.

When R in formula I is alkyl, it is preferably linear or branched $C_1$–$C_{12}$-, especially $C_1$–$C_8$- and more especially $C_1$–$C_4$-alkyl. Some examples are methyl, ethyl and the isomers of propyl, butyl, pentyl, hexyl, heptyl, octyl, nonyl, decyl, undecyl, dodecyl, tridecyl, tetradecyl, pentadecyl, hexadecyl, heptadecyl and octadecyl. Linear alkyl is also preferred.

When R in formula I is cycloalkyl, it is preferably $C_4$–$C_7$cycloalkyl, especially $C_5$- or $C_6$-cycloalkyl. Some examples are cyclopropyl, cyclobutyl, cyclopentyl, cyclohexyl, cycloheptyl and cyclooctyl.

When R in formula I is phenylalkyl, it is preferably benzyl or 1-phenyleth-2-yl.

In a preferred sub-group, R in formula I is H or is phenyl that is unsubstituted or substituted by $C_1$–$C_{18}$alkyl, $C_1$–$C_{18}$alkoxy, $R_3$—O—C(O)—, halogen, —CN or by —$NO_2$, $R_3$ being $C_1$–$C_{18}$alkyl, $C_3$–$C_8$cycloalkyl, phenyl, benzyl, $C_1$–$C_{12}$alkylphenyl or $C_1$–$C_{12}$alkylbenzyl.

$R_3$ is preferably $C_1$–$C_{12}$alkyl, especially $C_1$–$C_6$alkyl.

$R_1$ and $R_2$ as alkyl and alkoxy may be linear or branched and are preferably $C_1$–$C_8$alkyl or $C_1$–$C_8$alkoxy, more preferably $C_1$–$C_6$alkyl or $C_1$–$C_6$alkoxy and especially $C_1$–$C_4$alkyl or $C_1$–$C_4$alkoxy. Some examples are methyl, ethyl, n- and iso-propyl, n-, iso- or tert-butyl, pentyl, hexyl, methoxy, ethoxy, n- or iso-propoxy, n-, iso- or tert-butoxy, pentoxy and hexoxy.

An especially preferred sub-group of the compounds of formula I comprises those wherein Me is Pt(II), R is H or is phenyl that is unsubstituted or substituted by $C_1$–$C_{12}$alkyl, $C_1$–$C_{12}$alkoxy, $C_1$–$C_{18}$alkyl-O—C(O)—, F, Cl, Br, —CN or by —$NO_2$, and each of $R_1$ and $R_2$ is H.

A very especially preferred sub-group of the compounds of formula I comprises those wherein Me is Pt(II), R is H, phenyl or $C_1$–$C_4$alkylphenyl, and each of $R_1$ and $R_2$ is H.

The invention relates also to a process for the preparation of the compounds of formula I, which comprises reacting a compound of formula II

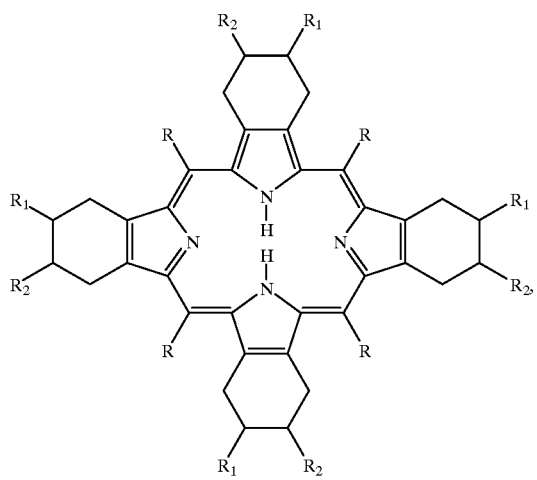

(II)

wherein

R, $R_1$ and $R_2$ are as defined for formula I.
with a palladium(II) or platinum(II) salt in the presence of an organic nitrile and, where appropriate, a solvent, at elevated temperatures.

Elevated temperatures may be, for example, from 50 to 300° C., preferably from 100 to 250° C., especially from 150 to 250° C. and more especially from 160 to 220° C.

The process can be carried out under normal pressure or elevated pressure. High pressure is advantageously used when low-boiling organic nitriles and/or solvents are employed.

The salts of Pd and Pt may be salts of inorganic or organic acids.

Examples of inorganic acids are hydrohalic acids (for example HCl, HBr and HI), oxy acids of carbon, sulfur, nitrogen and phosphorus (for example carbonic acid, sulfuric acid, sulfurous acid, nitric acid, phosphorous acid and phosphoric acid), and per acids, for example $HClO_4$ or $HBrO_4$. Preferred acids are hydrohalic acids, especially HCl.

Examples of organic acids are carboxylic acids and halocarboxylic acids (for example acetic acid, propionic acid, butyric acid, benzoic acid, phenylacetic acid, chlorobenzoic acid, trichloroacetic acid and trifluoroacetic acid), sulfonic acids and halosulfonic acids (for example methylsulfonic acid, ethylsulfonic acid, phenylsulfonic acid, p-toluenesulfonic acid, trichloromethylsulfonic acid, trifluoromethylsulfonic acid and chlorophenylsulfonic acid), and phosphonic acids and halophosphonic acids (for example methanephosphonic acid, phenylphosphonic acid, phenylphosphinic acid and trifluoromethylphosphonic acid).

In a preferred form, palladium and platinum halides are used as the palladium and platinum salts, especially $PdCl_2$ and $PtCl_2$.

Suitable organic nitriles are aliphatic, cycloaliphatic, heterocycloaliphatic, aromatic and heteroaromatic nitriles. They may contain from 2 to 20, preferably from 2 to 12 and especially from 2 to 8 carbon atoms, including the nitrile group. The organic nitrites preferably correspond to formula III

(III)

wherein $R_4$ is $C_1$–$C_{17}$alkyl, preferably $C_1$–$C_{11}$alkyl and especially $C_1$–$C_6$alkyl, unsubstituted or $C_1$–$C_4$alkyl- or $C_1$–$C_4$alkoxy-substituted $C_5$–$C_7$cycloalkyl, unsubstituted or $C_1$–$C_4$alkyl- or $C_1$–$C_4$alkoxy-substituted phenyl, naphthyl or phenyl-$C_1$–$C_4$alkyl.

Examples of alkyl and alkoxy, which may be linear or branched, have been mentioned hereinabove for R and $R_1$. $R_4$ as alkyl is preferably methyl, ethyl, propyl or butyl. $R_4$ as cycloalkyl is preferably cyclopentyl or cyclohexyl.

Preferred examples of $R_4$ are methyl, ethyl, propyl, butyl, cyclopentyl, cyclohexyl, phenyl, toluyl, xylyl, benzyl and methylbenzyl.

For the process according to the invention, preference is given to high-boiling nitrites, especially aromatic nitrites. Benzonitrile is very especially preferred.

The compounds of formula II and the palladium or platinum salts can be used in equimolar amounts, or an excess of the salts, for example up to twice the amount, can be used.

The nitrites are preferably used in a molar ratio of palladium or platinum salts to organic nitrile of at least 1:2. When an excess is used, the organic nitrile at the same time acts as solvent.

The reaction can be carried out in the presence of organic solvents or mixtures of solvents. The solvents are preferably dipolar and aprotic. Examples of solvents are ethers (dipropyl ether, dibutyl ether, ethylene glycol dimethyl or diethyl ether, diethylene glycol dimethyl ether, tetrahydrofuran and dioxane), N-dialkylated acid amides or N-alkylated lactams (dimethylformamide, dimethylacetamide, N-methylpyrrolidone, N-methylcaprolactam), sulfones and sulfoxides (tetramethylene sulfone and tetramethylene sulfoxide), esters and lactones (acetic acid octyl ester, butyrolactone, caprolactone, valerolactone), nitrites (acetonitrile, butyronitrile, benzonitrile, benzyinitrile), ketones (acetone, isopropyl methyl ketone), hydrocarbons (benzene, toluene, xylene) and halogenated hydrocarbons (methylene chloride, chloroform, 1,1,1-trichloroethane, 1,1,2,2-tetrachloroethane, chlorobenzene).

The process according to the invention can be carried out in the presence of basic compounds as acid acceptors. Known acid acceptors are, for example, alkali metal hydroxides and hydrogen carbonates (NaOH, KOH, $NaHCO_3$, $KHCO_3$), ammonia and primary, secondary and tertiary amines (trimethylamine, tributylamine, morpholine, piperidine and imidazole).

The process according to the invention can be carried out in various ways. For example, it is possible to place the compound of formula II and the palladium or platinum salts in an organic nitrile and, where appropriate, a solvent and then heat the mixture.

It has proved advantageous first to heat the palladium or platinum salts in an excess of an organic nitrile and, where appropriate, a solvent for some time (for example from 1 minute to 30 minutes) and then to add the compound of formula II and continue heating.

In another form, in a first step there is first prepared by reacting the palladium or platinum salts with an organic nitrile a dinitrile complex of the palladium or platinum salts having the general formula $X_2Me(nitrile)_2$, wherein Me is Pd or Pt and X is the anion of a monobasic acid, and the complex is isolated in customary manner (for example crystallisation and recrystallisation and washing) and, where appropriate, is purified. Then the complex is dissolved in a solvent, the compound of formula II is added, and the mixture is heated.

The reaction time may be from several minutes to a few hours, according to the process variant. As compared with the reaction with benzoporphyrins, the reaction times are very considerably shortened and yields of over 90% are achieved; in addition, pure products are obtained virtually directly and do not have to be purified before being used further. The reaction times are generally less than 8 hours.

Isolation of the crystalline products can be carried out, for example, by concentrating the reaction mixture by evaporation, extracting the residue by washing with a solvent, and then crystallising.

The compounds of formula II are known or can be prepared by analogous processes; see, for example, D. A. May et at, J. Org. Chem. 57 (1992), pages 4820 to 4821, and T. J. Aartsma et al., J. Am. Chem. Soc., Vol. 104, No. 23, pages 6278 to 6283.

Compounds of formula II can also be obtained in a manner known per se by reacting tetrahydroisoindolines of the formula

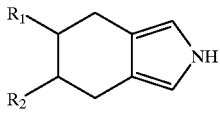

with an aldehyde of the formula

R—CHO to form a compound of the formula

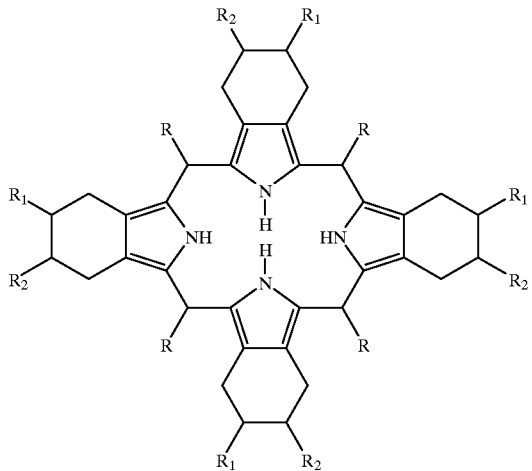

wherein $R_1$, $R_2$ and R are as defined for formula I, and then dehydrogenating those compounds in a known manner using dehydrogenating agents, for example chloranil, dichlorodicyanobenzoquinone, or catalytically using noble metal catalysts, to form the porphyrins of formula II

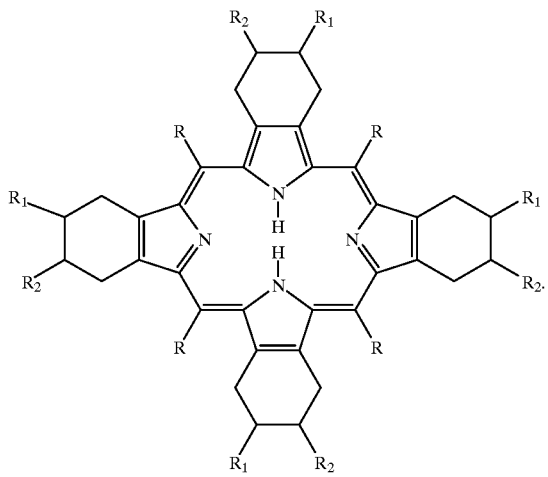

(II)

The compounds of formula I can be dehydrogenated to the benzoporphyrins surprisingly simply under mild reaction conditions and in short reaction times, in high yields and purities, although the cyclohexene ring is not activated. Accordingly, the compounds of formula I are valuable intermediates with which metal benzoporphyrins for use as phosphorescence indicators can be prepared directly and economically in large amounts in an industrial process.

The compounds of formula II accordingly have the great advantage that they are highly reactive with palladium or platinum salts and the metal complexes can readily be dehydrogenated to known palladium and platinum benzoporphyrins, so that, via a novel method of preparation, an economic process that can be used on an industrial scale is made available.

When R is not hydrogen, the compounds of formula II are novel intermediates. The invention relates also to compounds of formula IIa

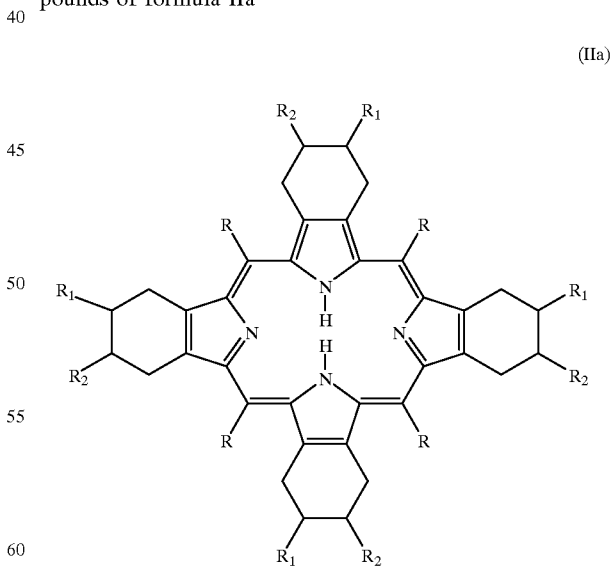

(IIa)

wherein

R is $C_1$–$C_{18}$alkyl, or is $C_3$–$C_8$cycloalkyl, phenyl, pyridyl or phenyl-$C_1$–$C_4$alkylene, each of which is unsubstituted or substituted by $C_1$–$C_{18}$alkyl, $C_1$–$C_{18}$alkoxy, $R_3$—O—C(O)—, halogen, —CN or by —$NO_2$;

$R_1$ and $R_2$ are each independently of the other H, $C_1$–$C_{12}$alkyl or $C_1$–$C_{12}$alkoxy, or $R_1$ and $R_2$ together are —OCH$_2$O—, —OCH$_2$CH$_2$O— or —CH=CH—CH=CH—; and $R_3$ is $C_1$–$C_{18}$alkyl, $C_3$–$C_8$cycloalkyl, phenyl, benzyl, $C_1$–$C_{12}$alkylphenyl or $C_1$–$C_{12}$alkylbenzyl.

The invention relates also to a process for the preparation of compounds of formula IV

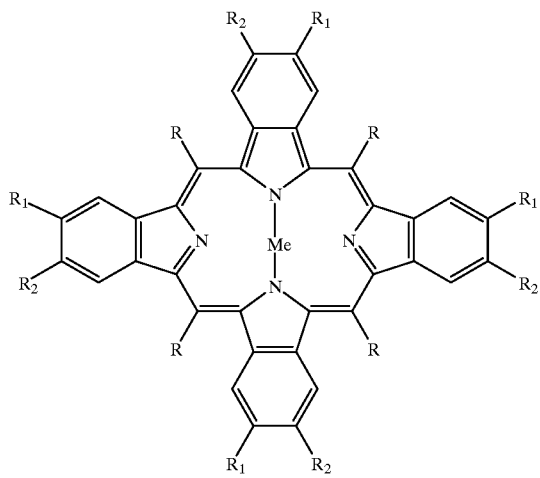

(IV)

wherein

Me, R, $R_1$ and $R_2$ are as defined for formula I which comprises dehydrogenating compounds of formula I

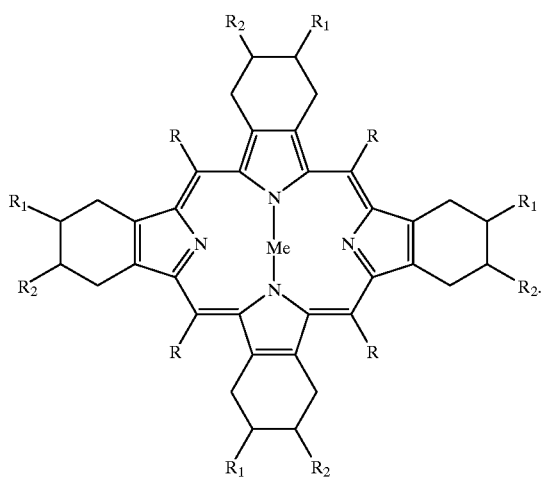

(I)

The second process according to the invention can be carried out under pressure or, preferably, under normal pressure.

The reaction temperatures may be from 30 to 250° C., preferably from 50 to 200° C. and especially from 100 to 200° C. The reaction is preferably carried out in the presence of solvents. The solvents mentioned hereinabove may be used. Preferred solvents are halogenated hydrocarbons and aromatic hydrocarbons (toluene and xylene).

The dehydrogenation can be carried out heterogeneously using, for example, platinum or palladium. It is, however, preferable to carry out the reaction homogeneously using organic dehydrogenating agents.

The organic dehydrogenating agents are preferably quinones and quinoid compounds having, for example, (NC)$_2$C= groups instead of the quinoid oxygen. The quinones and quinoid compounds are advantageously substituted by electron-attracting radicals, for example halogens, such as fluorine, chlorine or bromine, —NO$_2$ or —CN. Examples are benzoquinones, naphthoquinones and naphthacenediones or dicyanobenzodimethanes, each mono- or polysubstituted by F, Cl, Br or by —CN. Some specific examples are tetrachlorobenzoquinone (chloranil), dichlorodicyanobenzoquinone and tetrachlorodicyanobenzodimethane. Another suitable dehydrogenating agent is dichlorodicyanoquinoline.

The dehydrogenating agent is preferably added in equimolar amounts or in an excess.

The process is simple to carry out and can be effected, for example, as follows: the compound of formula I and the dehydrogenating agent are placed in a solvent and then heated with stirring.

Isolation of the crystalline compounds can be carried out in customary manner by removing the solvent and taking up the residue in a nonsolvent and filtering. The filtration residue can then be purified by means of recrystallisation or chromatographic methods.

Compounds of formula I are in themselves also excellent phosphorescence indicators for the determination of oxygen in gases or liquids, since they have a surprisingly high quantum yield and a long lifetime in the excited state. Furthermore, they are distinguished by good light stabilities, which also means a correspondingly long usable life. On account of the long-wave phosphorescence in the NIR range, measurements can even be carried out in cloudy liquids or gases. Moreover, the compounds of formula I are very readily soluble in many organic solvents, so that the preparation of sensors by dissolving the compounds of formula I together with an oxygen-permeable and membrane-forming polymer and then applying the solution to a support material is possible without difficulty using customary coating processes, for example spin-casting. The compounds of formula I can thus be distributed uniformly in the polymer membrane.

Accordingly, the invention relates also to a composition comprising a) an effective amount of a compound of formula I wherein R is H or $C_1$–$C_{18}$alkyl, or is $C_3$–$C_8$cycloalkyl or phenyl-$C_1$–$C_4$alkylene, each of which is unsubstituted or substituted by $C_1$–$C_{18}$alkyl, $C_1$–$C_{18}$alkoxy, $R_3$—O—C(O)—, halogen, —CN or by —NO$_2$, b) an oxygen-permeable and membrane-forming polymer, and c) an organic solvent for components a) and b).

Suitable solvents have been mentioned hereinabove. The choice of solvents is guided essentially by the solubility properties of the polymers.

"Effective amount" means a concentration of compound of formula I that is sufficient to detect the extinction of phosphorescence on contact with oxygen. The concentration of compound of formula I can be, for example, from 0.01 to 20% by weight, preferably from 0.1 to 10% by weight, especially from 0.5 to 5% by weight and more especially from 0.5 to 3% by weight, based on the amount of components a) and b).

The polymers may be selected from natural, modified natural and synthetic polymers. The polymers are to have a suitable oxygen permeability for the field of application of the sensor; for example, for the trace analysis of oxygen a polymer having a high oxygen permeability is required in order to achieve the necessary high sensitivity and low detection threshold of the sensor, whereas for the detection of oxygen in body fluids, for example, a moderate permeability is suitable, which leads to a measuring range of the sensor in the physiological range and still achieves adequate sensitivity in that range. Furthermore, it is advantageous for the polymers to be hydrophobic on application of aqueous analytes in order to avoid the establishment of equilibria by swelling, which does not, however, play a significant role in the analysis of gas mixtures.

Examples of polymers are carbohydrates, such as cellulose, cellulose acetate, homo- and co-polymers based on styrene, acrylonitrile, acrylic acid esters, methacrylic acid esters, acrylamides, methacrylamides, vinyl ethers and olefins, polyacetylenes, polyamides, polyesters and polyurethanes. The polymers and their membrane properties are familiar to the person skilled in the art, and the suitable polymers can be determined by simple tests.

Preferred polymers are polystyrene, copolymers of styrene and acrylonitrile, polyacrylates and polymethacrylates, and copolymers of acrylates and/or methacrylates with acrylonitrile. The acrylates and methacrylates can contain linear or branched $C_1$–$C_{18}$- and preferably $C_1$–$C_{12}$-alkyl radicals in the ester groups, for example methyl, ethyl, butyl, pentyl, hexyl, heptyl, octyl, nonyl, decyl, undecyl or dodecyl. The acrylates and methacrylates can be copolymers of monomers that contain different alkyl radicals in the ester groups.

The compositions according to the invention can be prepared by dissolving components a) and b) in a solvent, where appropriate with heating. By means of the concentration and nature of the polymer, its molecular weight and the choice of solvent, the viscosity of the composition can be so adjusted that the desired layer thickness is achieved in the preparation of optrodes.

The invention relates also to a composition comprising
a) a solid support material to which there is applied a layer of
b) an oxygen-permeable polymer in which there is uniformly distributed
c) a compound of formula I wherein R is H or $C_1$–$C_{18}$alkyl, or is $C_3$–$C_8$cycloalkyl or phenyl-$C_1$–$C_4$alkylene, each of which is unsubstituted or substituted by $C_1$–$C_{18}$alkyl, $C_1$–$C_{18}$alkoxy, $R_3$—O—C(O)—, halogen, —CN or by —$NO_2$.

The support materials can be transparent, translucent or opaque materials, with transparent materials being preferred. Examples of materials are plastics, glasses, minerals, metal and semi-metal oxides, metal nitrides, and metal and semi-metal carbides. Preferred support materials are inorganic and organic glasses as well as plastics.

The surface area of the support material can be in the range of, for example, $mm^2$ to $cm^2$, preferably from 1 $mm^2$ to 10 $cm^2$, especially from 2 $mm^2$ to 5 $cm^2$, more especially from 5 $mm^2$ to 5 $cm^2$. In order to carry out multiple measurements there may be arranged on the support several, for example from 2 to 30 and preferably from 2 to 20, polymer layers that are separate from one another and have been produced, for example, by means of screen printing or writing processes. For the sensors, the glass wafers can be cut into strips. The sensor area effectively used can be approximately from 0.8 to 20 $mm^2$.

The layer thickness of the composition comprising the polymer and the compound of formula I can be, for example, from 0.5 to 1000 µm, preferably from 0.5 to 200 µm, especially from 0.5 to 50 µm and more especially from 0.5 to 5 µm.

The concentration of compound of formula I can be, for example, from 0.01 to 20% by weight, preferably from 0.1 to 10% by weight, especially from 0.5 to 5% by weight and more especially from 0.5 to 3% by weight, based on the amount of components a) and b). Bonding layers may be located between the polymer layer and the support material.

The composition according to the invention can be prepared by known coating processes, for example spreading, knife application, writing, pouring, for example curtain pouring processes or, especially, spin-casting.

The composition according to the invention is excellently suitable for the detection of oxygen when the active layer is in contact with an analyte, which may be gaseous or liquid. The composition is especially suitable for human and animal diagnostics.

The invention relates also to a method of determining oxygen in an analyte, in which an oxygen-sensitive layer of an optical sensor, which layer contains a luminescence indicator and an oxygen-permeable polymer, is irradiated with light and luminescence radiation is produced, then the analyte is brought into contact with the layer and the reduction in the intensity of the luminescence radiation in dependence upon the oxygen content is detected, wherein the oxygen-sensitive layer comprises an effective amount of a compound of formula I wherein R is H or $C_1$–$C_{18}$alkyl, or is $C_3$–$C_8$cycloalkyl or phenyl-$C_1$–$C_4$alkylene, each of which is unsubstituted or substituted by $C_1$–$C_{18}$alkyl, $C_1$–$C_{18}$alkoxy, $R_3$—O—C(O)—, halogen, —CN or by —$NO_2$.

The preferences and preferred forms indicated hereinabove for the two compositions apply also to the method according to the invention.

Suitable radiation sources for exciting the luminescence are, for example, UV lamps (halogen and xenon lamps), light-emitting diodes, lasers and diode lasers. It may be advantageous to select, by means of filters, light of the wavelength at which the luminescence dye has an absorption maximum.

The luminescence light emitted by the sensors can be collected, for example using a lens system, and then fed to a detector. There may be used as detectors photoelectron multipliers or photodiodes. The lens system may be so arranged that the luminescence radiation is measured through a transparent support. Advantageously, the radiation is deflected via a dichroic mirror and, by means of filters, light of the wavelength at which the luminescence dye has an emission maximum is selected. The measurements are advantageously carried out during contact with the calibrating solutions or sample solutions or gas samples. For quantitative measurements, the sensors are calibrated using samples having a known oxygen content. The measurements can be carried out in fluorescence spectrometers, which are commercially available.

The oxygen detection can be carried out discontinuously in individual cells or continuously in flow-through systems; using the stop/flow method it is possible to carry out a measurement repeatedly or to measure different analytes in succession. Parallel measurements are also possible if multi-channel systems are used.

The invention relates also to the use of compounds of formula I wherein R is H or $C_1$–$C_{18}$alkyl, or is $C_3$–$C_8$cycloalkyl or phenyl-$C_1$-$C_4$alkylene, each of which is unsubstituted or substituted by $C_1$–$C_{18}$alkyl, $C_1$–$C_1$alkoxy, $R_3$—O—C(O)—, halogen, —CN or by —$NO_2$ as luminescence indicators, especially for the optical determination of oxygen.

The Examples which follow illustrate the invention in greater detail.

A) Preparation of Starting Materials

EXAMPLE A1

Preparation of $Cl_2Pt(C_6H_5\text{—}CN)_2$ 1.0 g of $PtCl_2$ is dissolved in 200 ml of hot, freshly distilled benzonitrile, and the solution is subsequently filtered and then concentrated to dryness by evaporation in vacuo. The residue is taken up in methanol, and the mixture is filtered and dried in vacuo. 1.63 g (92%) of yellowish crystals are obtained.

EXAMPLE A2

Preparation of

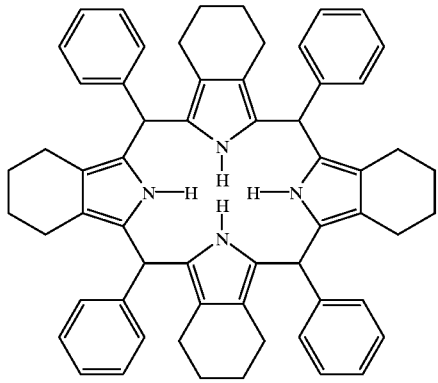

At room temperature and with stirring, 0.5 ml of benzaldehyde and 0.6 g of the isoindoline of the formula

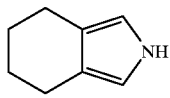

are dissolved in 500 ml of $CH_2Cl_2$, and the reaction solution is freed of oxygen for a period of 15 minutes by means of a stream of argon gas. Then 0.062 ml of boron trifluoride etherate is added and the solution is stirred for one hour with the exclusion of light. The solution is then concentrated by evaporation and the residue is made to crystallise with methanol and filtered off over a frit. Recrystallisation from $CH_2Cl_2$ is carried out. Yield 0.75 g. Melting point 217–220° C.

EXAMPLE A3

Preparation of

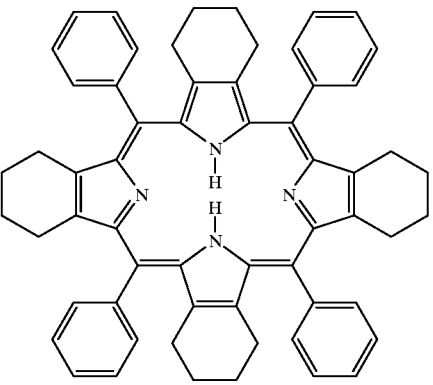

10.2 g of the compound according to Example A2 are dissolved in 2.2 liters of $CH_2Cl_2$, and 12.6 g of dichlorodicyanobenzoquinone are added thereto. After one hour at reflux, the organic phase is washed with 1N NaOH and concentrated aqueous NaCl. After concentration by evaporation, the residue is chromatographed over Alox B Act. 1 with chloroform. Yield 9.7 g.

B) Preparation of platinum cyclohexenoporphyrins

EXAMPLE B1

Preparation of platinum(II) cyclohexenoporphyrin

A mixture of 1.0 g (1.9 mmol) of tetracyclohexenoporphyrin, 2 g of $Cl_2Pt(C_6H_5CN)_2$ (4.2 mmol) and 200 ml of freshly distilled benzonitrile is heated at reflux for 2 hours, with stirring. Then the mixture is left to stand overnight at room temperature and the precipitate that forms is isolated by filtration. Drying is carried out overnight in vacuo at 100° C., and 1.27 g (92%) of a dark-red microcrystalline powder are obtained.

Absorption spectrum in $CHCl_3$, $\lambda_{max}(\epsilon)$: 380 (266400), 501 (11000) and 536 (54900).

$^1$H-NMR (500 MHz, $CHCl_3$): 9.86 (4H, s, broad); 4.10 (16H, s, broad) and 2.50 (16H, s).

Phosphorescence quantum yields: $\phi_0$ (in degassed $CHCl_3$): 0.421
$\phi$ (in air-saturated $CHCl_3$): 0.0011.

EXAMPLE B2

Preparation of platinum(II) tetracyclohexenotetraphenylporphyrin 2.5 g of the porphyrin according to Example A3 and 1.2 g of $PtCl_2$ are heated at reflux in 450 ml of benzonitrile for 6.5 hours, with stirring. After cooling, the mixture is concentrated by evaporation and the residue is taken up in 20 ml of $CH_2Cl_2$ and left to stand overnight. The crystals that form are isolated by filtration and dried in vacuo. Yield 2.3 g (86%).

Absorption spectrum in $CHCl_3$, $\lambda_{max}(\epsilon)$: 560 (16640), 526 (14030) and 412 (182000).

$^1$H-NMR (500 MHz, $CHCl_3$): 8.06 (8H, m, aromatic); 7.63 (12H, m, aromatic), 2.30 (16H, s, 8 $CH_2$) and 1.45 (16H, s, 8 $CH_2$).

COMPARISON EXAMPLE

Over a period of 48 hours, 0.1 g of tetraphenylporphyrin is added slowly to a solution, maintained at reflux (200° C.), of $PtCl_2$ in 125 ml of benzonitrile. Then the mixture is left to stand overnight at room temperature, and the precipitate that forms is isolated by filtration. Drying is carried out overnight in vacuo at 100° C., and a black microcrystalline powder is obtained in a yield of only 6.5%.

C) Preparation of platinum(II) benzoporphyrins

Example C1

Preparation of platinum(II) tetrabenzoporphyrin

A mixture of 800 mg (1.1 mmol) of platinum(II) cyclohexenoporphyrin according to Example B1, 2.25 g (10 mmol) of dichlorodicyanoquinoline and 600 ml of freshly distilled benzonitrile is heated at 100° C. for 4 hours, with stirring. Then the mixture is concentrated in vacuo to a volume of about 75 ml and is left to stand overnight. The precipitate that forms is subsequently isolated by filtration, washed with methanol and chloroform and then dried. There are obtained 1.05 g of crude product, which is heated for 24 hours at 0.04 torr and 250° C. in order to remove readily volatile fractions.

| | |
|---|---|
| Absorption spectrum in $CHCl_3$, $\lambda_{max}(\epsilon)$: | 394 (24950), 595 (19730). |
| Phosphorescence quantum yields: | $\phi_0$ (in degassed $CHCl_3$): 0.21 |
| | $\phi$ (in air-saturated $CHCl_3$): 0.0045. |

EXAMPLE C2

Preparation of platinum(I) tetraphenyltetrabenzoporphyrin 2.0 g (2 mmol) of platinum(II) tetraphenylcyclohexenoporphyrin according to Example B2 are mixed with 4.5 g (20 mmol) of 2,3-dichloro-5,6-dicyano-1,4-benzoquinone and 400 ml of toluene, and the mixture is heated at reflux for one hour. After cooling, the reaction mixture is taken up in methanol and filtered. There are obtained 1.8 g of crude product, which is dissolved in chloroform and then subjected to flash chromatography on silica gel. The green eluates are combined and the chloroform is removed in vacuo at 60° C. 1.4 g (71%) of a microcrystalline green powder are obtained.

Absorption spectrum in $CHCl_3$, $\lambda_{max}(\epsilon)$: 615 (88120), 566 (11650) and 431 (150000).

$^1$H-NMR (500 MHz, $CHCl_3$): 8.26 (8H, m, aromatic); 7.93 (4H, m, aromatic), 7.87 and 7.18 (16H, m, $A_2B_2$, aromatic).

| | |
|---|---|
| Phosphorescence quantum yields: | $\phi_0$ (in degassed $CHCl_3$): 0.19 |
| | $\phi$ (in air-saturated $CHCl_3$): 0.004. |
| Lifetime in degassed $CHCl_3$: 38.1 µs. | |

D) Preparation of Coating Compositions

EXAMPLE D1

An approximately 0.1% saturated solution of platinum(I) tetracyclohexenoporphyrin (Example B1) in chloroform is first prepared. Then 50 mg of a copolymer of 55 mol % styrene and 45 mol % acrylonitrile are dissolved in 2 g of that dye solution (2.5% copolymer). The concentration of dye is approximately 2% by weight, based on the polymer.

EXAMPLE D2

An approximately 0.1% saturated solution of platinum(II) tetracyclohexenoporphyrin (Example B1) in chloroform is first prepared. Then 50 mg of a copolymer of 10 mol % ethylhexyl acrylate, 45 mol % methyl methacrylate and 45 mol % acrylonitrile are dissolved in 2 g of that dye solution (2.5% polymer). The concentration of dye is approximately 2% by weight, based on the polymer.

E) Preparation of Sensors

EXAMPLE E1

150 µl of the solution according to Example D1 are applied to a silanised glass plate by means of spin-casting at 3000 revolutions/minute under a chloroform atmosphere, and then the sensor is dried in an oven at 80° C. under a nitrogen atmosphere for at least two hours.

EXAMPLE E2

150 µl of the solution according to Example D2 are applied to a silanised glass plate by means of spin-casting at 3000 revolutions/minute under a chloroform atmosphere, and then oven at 80° C. under a nitrogen atmosphere for at least two hours.

F) Application Examples

EXAMPLE F1

Oxygen detection using platinum(II) tetracyclohexenoporphyrin

The support is so arranged that the excitation radiation falls on the active layer at an oblique angle. The radiation source used is a green light-emitting diode with the interposition of a shortpass interference filter (KIF, Schott-Schleifer AG) which exhibits maximum transmission ($\lambda_{max}$) at wavelength of 533.5 nm and 50% transmission ($\lambda_{Kant}$) at a wavelength of 566.5 nm. A 645 DF 20 band filter (G+P Electronic AG) is used as the emission filter. The phosphorescence radiation is measured using a photodiode having an amplification of $10^{11}$. There is used as the measurement sample a sodium chloride-containing phosphate buffer [PBS, ionic strength 0.1 M (NaCl)] which has an oxygen partial pressure of 0, 80 and 160 torr. The result is shown the following Tables.

Measurement using the sensor according to Example E1:

| Fluorescence intensity (mV) | $O_2$ partial pressure (torr) |
|---|---|
| 448 | 0 |
| 232 | 80 |
| 168 | 160 |

Measurement using the sensor according to Example E2:

| Fluorescence intensity (mV) | $O_2$ partial pressure (torr) |
|---|---|
| 140 | 0 |
| 100 | 80 |
| 83 | 160 |

What is claimed is:

1. A compound of formula I

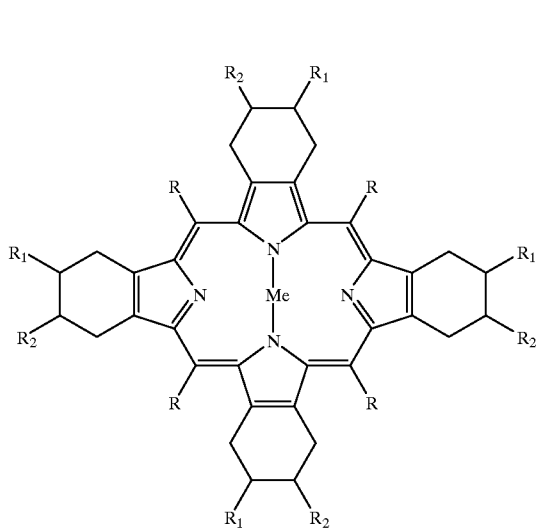

(I)

wherein

Me is Pd(II) or Pt(II);

R is H or $C_1$–$C_{18}$alkyl, or is $C_3$–$C_8$cycloalkyl, phenyl, pyridyl or phenyl-$C_1$–$C_4$alkylene, each of which is unsubstituted or substituted by $C_1$–$C_{18}$alkyl, $C_1$–$C_{18}$alkoxy, $R_3$—O—C(O)—, halogen, —CN or by —$NO_2$;

$R_1$ and $R_2$ are each independently of the other H, $C_1$–$C_{12}$alkyl or $C_1$–$C_{12}$alkoxy, or $R_1$ and $R_2$ together are —$OCH_2O$—, —$OCH_2CH_2O$— or —CH=CH—CH=CH—; and $R_3$ is $C_1$–$C_{18}$alkyl, $C_3$–$C_8$cycloalkyl, phenyl, benzyl, $C_1$–$C_{12}$alkylphenyl or $C_1$–$C_{12}$alkylbenzyl.

2. A compound according to claim 1, wherein Me is Pt.

3. A compound according to claim 1, wherein R in formula I is H or is phenyl that is unsubstituted or substituted by $C_1$–$C_{18}$alkyl, $C_1$–$C_{18}$alkoxy, $R_3$—O—C(O)—, halogen, —CN or by —$NO_2$, $R_3$ being $C_1$–$C_{18}$alkyl, $C_3$–$C_8$cycloalkyl, phenyl, benzyl, $C_1$–$C_{12}$alkylphenyl or $C_1$–$C_{12}$alkylbenzyl.

4. A compound according to claim 1, wherein the compound of formula I is a compound wherein Me is Pt(II), R is H or is phenyl that is unsubstituted or substituted by $C_1$–$C_{12}$alkyl, $C_1$–$C_{12}$alkoxy, $C_1$–$C_{18}$alkyl-O—C(O)—, F, Cl, Br, —CN or by —$NO_2$, and each of $R_1$ and $R_2$ is H.

5. A compound according to claim 1, wherein the compound of formula I is a compound wherein Me is Pt(II), R is H, phenyl or $C_1$–$C_4$alkylphenyl, and each of $R_1$ and $R_2$ is H.

6. A process for the preparation of a compound of formula I as claimed in claim 1, wherein the process comprises reacting a compound of formula II

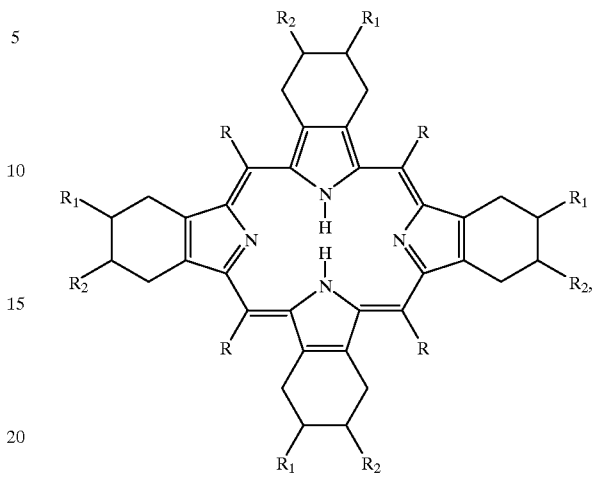

(II)

wherein

R, $R_1$ and $R_2$ are as defined for formula I in claim 1, with a palladium (II) or platinum (II) salt in the presence of an organic nitrile and, where appropriate, a solvent, at a temperature of from 50 to 300° C.

7. A process according to claim 6, wherein palladium and platinum halides are used as the palladium and platinum salts.

8. A process according to claim 6, wherein aliphatic, cycloaliphatic, heterocycloaliphatic, aromatic and heteroaromatic nitrites are used as the organic nitriles.

9. A process according to claim 6, wherein the organic nitrites correspond to formula III $$R_4\text{—CN} \quad \text{(III)}$$

wherein $R_4$ is $C_1$–$C_{17}$alkyl, unsubstituted or $C_1$–$C_4$alkyl- or $C_1$–$C_4$alkoxy-substituted $C_5$–$C_7$cycloalkyl, unsubstituted or $C_1$–$C_4$alkyl- or $C_1$–$C_4$alkoxy-substituted phenyl, naphthyl or phenyl-$C_1$–$C_4$alkyl.

10. A process according to claim 6, wherein the molar ratio of palladium or platinum salts to organic nitrile is at least 1:2.

11. A process according to claim 6, wherein in a preliminary step the palladium or platinum salts are heated in an excess of an organic nitrile and, where appropriate, a solvent, and then the compound of formula II is added and heating is continued.

12. A process according to claim 6, wherein in a first step there is first prepared by reacting the palladium or platinum salts with an organic nitrile a dinitrile complex of the palladium or platinum salts having the general formula $X_2$Me(nitrile)$_2$, wherein Me is Pd or Pt and X is the anion of a monobasic acid, the complex is subsequently dissolved in a solvent, and then the compound of formula II is added and the mixture is heated.

13. A composition comprising a) a compound of formula I according to claim 1 wherein R is H or $C_1$–$C_{18}$alkyl, or is $C_3$–$C_8$cycloalkyl or phenyl-$C_1$–$C_4$alkylene, each of which is unsubstituted or substituted by $C_1$–$C_{18}$alkyl, $C_1$–$C_{18}$alkoxy, $R_3$—O—C(O)—, halogen, —CN or by —$NO_2$, in an amount sufficient to detect the extinction of phosphorescence on contact with oxygen, b) an oxygen-permeable and membrane-forming polymer, and c) an organic solvent for components a) and b).

14. A composition according to claim 13, wherein the polymers are polystyrene, copolymers of styrene and acrylonitrile, polyacrylates and polymethacrylates, or copolymers of acrylates and/or methacrylates with acrylonitrile.

15. A composition comprising a) a solid support material to which there is applied a layer of b) an oxygen-permeable polymer in which there is uniformly distributed c) a compound of formula I according to claim 1 wherein R is H or $C_1$–$C_{18}$alkyl, or is $C_3$–$C_8$cycloalkyl or phenyl-$C_1$–$C_4$alklyene, each of which is unsubstituted or substituted by $C_1$–$C_{18}$alkyl, $C_1$–$C_{18}$alkoxy, $R_3$—O—C(O)—, halogen, —CN or by —$NO_2$.

16. A method of determining oxygen in an analyte, in which an oxygen-sensitive layer of an optical sensor, which layer contains a luminescence indicator and an oxygen-permeable polymer, is irradiated with light and luminescence radiation is produced, then the analyte is brought into contact with the layer and the reduction in the intensity of the luminescence radiation in dependence upon the oxygen content is detected, wherein the oxygen-sensitive layer comprises a compound of formula I as claimed in claim 1 wherein R is H or $C_1$–$C_{18}$alkyl, or is $C_3$–$C_8$cycloalkyl or phenyl-$C_1$–$C_4$alkylene, each of which is unsubstituted or substituted by $C_1$–$C_{18}$alkyl, $C_1$–$C_{18}$alkoxy, $R_3$—O—C(O)—, halogen, —CN or by —$NO_2$ in an amount sufficient to detect the extinction of phosphorescence on contact with oxygen.

17. A process according to claim 9, wherein $R_4$ is $C_1$–$C_{11}$alkyl.

18. A process according to claim 17, wherein $R_4$ is $C_1$–$C_6$alkyl.

* * * * *